United States Patent
Watanabe et al.

(10) Patent No.: US 8,592,417 B2
(45) Date of Patent: *Nov. 26, 2013

(54) 2-SUBSTITUTED-6-HETEROCYCLIC PYRIMIDONE DERIVATIVES AS TAU PROTEIN KINASE 1 INHIBITORS

(75) Inventors: Kazutoshi Watanabe, Kanagawa (JP); Toshiyuki Kohara, Kanagawa (JP); Kenji Fukunaga, Kanagawa (JP); Fumiaki Uehara, Kanagawa (JP)

(73) Assignees: Mitsubishi Tanabe Pharma Corporation, Osaka (JP); Sanofi, Paris (FR)

( * ) Notice: Subject to any disclaimer, the term of this patent is extended or adjusted under 35 U.S.C. 154(b) by 603 days.

This patent is subject to a terminal disclaimer.

(21) Appl. No.: 12/518,997

(22) PCT Filed: Dec. 26, 2007

(86) PCT No.: PCT/JP2007/075380
§ 371 (c)(1), (2), (4) Date: Sep. 21, 2009

(87) PCT Pub. No.: WO2008/078837
PCT Pub. Date: Jul. 3, 2008

(65) Prior Publication Data
US 2010/0113775 A1 May 6, 2010

(30) Foreign Application Priority Data
Dec. 26, 2006 (JP) .................. 2006-357476

(51) Int. Cl.
*A61K 31/535* (2006.01)
*C07D 413/14* (2006.01)

(52) U.S. Cl.
USPC ........................ 514/235.8; 544/123

(58) Field of Classification Search
USPC ........................ 544/123; 514/235.8
See application file for complete search history.

(56) References Cited

U.S. PATENT DOCUMENTS

| | | |
|---|---|---|
| 7,256,199 B1 | 8/2007 | Watanabe et al. |
| 7,427,615 B2 | 9/2008 | Uehara et al. |
| 7,572,793 B2 | 8/2009 | Uehara et al. |
| 8,288,383 B2 | 10/2012 | Sakai et al. |
| 2009/0124618 A1 | 5/2009 | Watanabe et al. |
| 2009/0156804 A1 | 6/2009 | Okuyama et al. |
| 2009/0233918 A1 | 9/2009 | Fukunaga et al. |
| 2009/0239864 A1 | 9/2009 | Watanabe et al. |

FOREIGN PATENT DOCUMENTS

| | | |
|---|---|---|
| CN | 1328552 | 12/2001 |
| CN | 1555367 | 12/2004 |
| JP | 2002-525366 | 8/2002 |
| JP | 2005-510472 | 4/2005 |
| JP | 2005-510506 | 4/2005 |
| JP | 2006-521370 | 9/2006 |
| WO | 00/18758 A1 | 4/2000 |
| WO | 01/70728 A1 | 9/2001 |
| WO | WO 03/027080 * | 4/2003 |
| WO | 03/037888 | 5/2003 |
| WO | 2004/085408 | 10/2004 |
| WO | 2006/028290 A1 | 3/2006 |
| WO | 2006/036015 A2 | 4/2006 |
| WO | 2006/036015 A3 | 4/2006 |

OTHER PUBLICATIONS

Golub et al., Science, 286:531-537 (1999).*
Lala et al., Cancer and Metastasis Reviews, 17:91-106 (1998).*
Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimers[Online], [retrieved on Sep. 23, 2003]. Retrieved from the internet, URL:hyyp;//www.cnn.com/2003/HEALTH/conditions/09/24/alzheimers.drug.ap/index.html>.*
Mandel et al. CNS Drugs, 2003: 17(10); 729-62.*
Chinese Office action issued with respect to patent family member Chinese Patent Application No. 200780048375.3, dated Aug. 15, 2011, along with an English translation thereof.
Cohen et al., "Nature Reviews vol. 3, Issue 6, Jun. 2004, p. 479-487".

(Continued)

*Primary Examiner* — Rebecca Anderson
(74) *Attorney, Agent, or Firm* — Greenblum & Bernstein, P.L.C.

(57) ABSTRACT

A compound represented by the formula (I), an optically active isomer thereof, or a pharmaceutical acceptable salt thereof: wherein each $R^1$ represents hydrogen atom or the like; X represents oxygen atom or the like; A represents a $C_3$-$C_7$ cycloalkyl group, a $C_6$-$C_{10}$ aryl group or a heterocyclic group; $R^6$ represents a halogen atom or the like; s represents 0 or an integer of 1 to 5; Q represents a pyridine ring which may be substituted or pyrimidine ring; and $R^2$ represents hydrogen atom or the like, which is used for preventive and/or therapeutic treatment of a disease caused by abnormal activity of tau protein kinase 1 such as a neurodegenerative diseases (e.g. Alzheimer disease).

2 Claims, No Drawings

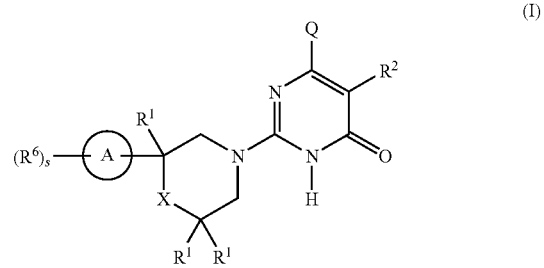

(I)

(56) References Cited

OTHER PUBLICATIONS

Meijer et al., "Trends in Pharmacological Sciences vol. 25 No. 9, Sep. 2004, p. 471-480".
Bhat et al., "Journal of Neurochemistry 2004, 89, 1313-1317".
Martinez et al., "Medicinal Research Reviews, vol. 22, No. 4, 373-384, 2002".
Carmichael et al., "Journal of Biological Chemistry Vo. 277, No. 37, Sep. 13, pp. 33791-33798, 2002".
Pérez et al., "Biochem. J. 372, p. 129-136, 2003".
Koh et al., "European Journal of Neuroscience, vol. 22, pp. 301-309, 2005".
Sato et al., "Nature Medicine 10, p. 55-63, 2004".
Droucheau et al., "Biochimica et Biophysica Acta 1967, 181-196, 2004".
International Preliminary Report on Patentability including Written Opinion for International Application No. PCT/JP2007/075380. 2009.
International Search Report for International Application No. PCT/JP2007/075380. 2008.
Official Action dated Dec. 11, 2012 in Japanese Patent Application No. 2009-525814 with English Language Excerption.

* cited by examiner

2-SUBSTITUTED-6-HETEROCYCLIC PYRIMIDONE DERIVATIVES AS TAU PROTEIN KINASE 1 INHIBITORS

TECHNICAL FIELD

The present invention relates to compounds that are useful as an active ingredient of a medicament for preventive and/or therapeutic treatment of diseases mainly caused by abnormal activity of tau protein kinase 1, such as neurodegenerative diseases (e.g. Alzheimer disease).

BACKGROUND ART

GSK3β (glycogen synthetase kinase 3β) is a proline directed serine, threonine kinase that plays an important role in the control of metabolism, differentiation and survival. It was initially identified as an enzyme which is able to phosphorylate and hence inhibit glycogen synthetase. It was later recognized that GSK3β was identical to tau protein kinase 1 (TPK1), an enzyme that phosphorylates tau protein in epitopes that are also found to be hyperphosphorylated in Alzheimer's disease and in several taupathies.

Interestingly, protein kinase B (AKT) phosphorylation of TPK1 results in a loss of its kinase activity, and it has been hypothesized that this inhibition may mediate some of the effects of neurotrophic factors. Moreover, phosphorylation by TPK1 of β-catenin, a protein involved in cell survival, results in its degradation by an ubiquitinilation dependent proteasome pathway.

Thus, it appears that inhibition of TPK1 activity may result in neurotrophic activity. Indeed there is evidence that lithium, an uncompetitive inhibitor of TPK1, enhances neuritogenesis in some models and also increases neuronal survival, through the induction of survival factors such as Bcl-2 and the inhibition of the expression of proapoptotic factors such as P53 and Bax.

Recent studies have demonstrated that β-amyloid increases the TPK1 activity and tau protein phosphorylation. Moreover, this hyperphosphorylation as well as the neurotoxic effects of β-amyloid are blocked by lithium chloride and by a TPK1 antisense mRNA. These observations strongly suggest that TPK1 may be the link between the two major pathological processes in Alzheimer's disease: abnormal APP (Amyloid Precursor. Protein) processing and tau protein hyperphosphorylation.

Although tau hyperphosphorylation results in a destabilization of the neuronal cytoskeleton, the pathological consequences of abnormal TPK1 activity are, most likely, not only due to a pathological phosphorylation of tau protein because, as mentioned above, an excessive activity of this kinase may affect survival through the modulation of the expression of apoptotic and antiapoptotic factors. Moreover, it has been shown that β-amyloid-induced increase in TPK1 activity results in the phosphorylation and, hence the inhibition of pyruvate dehydrogenase, a pivotal enzyme in energy production and acetylcholine synthesis.

Altogether these experimental observations indicate that TPK1 may find application in the treatment of the neuropathological consequences and the cognitive and attention deficits associated with Alzheimer's disease, as well as other acute and chronic neurodegenerative diseases and other pathologies where TPK1 is deregulated (Nature reviews Vol. 3, June 2004, p. 479-487; Trends in Pharmacological Sciences Vol. No. 9, September 2004, p. 471-480; Journal of neurochemistry 2004, 89, 1313-1317; Medicinal Research Reviews, Vol. 22, No. 4, 373-384, 2002).

The neurodegenerative diseases include, in a non-limiting manner, Parkinson's disease, tauopathies (e.g. Fronto temporal dementia, corticobasal degeneration, Pick's disease, progressive supranuclear palsy), Wilson's disease, Huntington's disease (The Journal of biological chemistry Vol. 277, No. 37, Issue of September 13, pp. 33791-33798, 2002), Prion disease (Biochem. J. 372, p. 129-136, 2003) and other dementia including vascular dementia; acute stroke and others traumatic injuries; cerebrovascular accidents (e.g. age related macular degeneration); brain and spinal cord trauma; amyotrophic lateral sclerosis (European Journal of Neuroscience, Vol. 22, pp. 301-309, 2005) peripheral neuropathies; retinopathies and glaucoma. Recent studies have also shown that inhibition of TPK1 results in neuronal differentiation of embryonic stem cells (ESC) and support the renewal of human and mouse ESCs and the maintenance of their pluripotency. This suggests that inhibitors of TPK1 could have applications in regenerative medicine (Nature Medicine 10, p. 55-63, 2004).

Inhibitors of TPK1 may also find application in the treatment of other nervous system disorders, such as bipolar disorders (manic-depressive illness). For example lithium has been used for more than 50 years as a mood stabilizer and the primary treatment for bipolar disorder. The therapeutic actions of lithium are observed at doses (1-2 mM) where it is a direct inhibitor of TPK1. Although the mechanism of action of lithium is unclear, inhibitors of TPK1 could be used to mimic the mood stabilizing effects of lithium. Alterations in Akt-TPK1 signaling have also been implicated in the pathogenesis of schizophrenia.

In addition, inhibition of TPK1 could be useful in treating cancers, such as colorectal, prostate, breast, non-small lung carcinoma, thyroid cancer, T or B-cell leukaemia and several virus-induced tumours. For example, the active form of TPK1 has been shown to be elevated in the tumors of colorectal cancer patients and inhibition of TPK1 in colorectal cancer cells activates p53-dependent apoptosis and antagonises tumor growth. Inhibition of TPK1 also enhances TRAIL-induced apoptosis in prostate cancer cell lines. TPK1 also plays a role in the dynamics of the mitototic spindle and inhibitors of TPK1 prevent chromosome movement and lead to a stabilization of microtubules and a prometaphase-like arrest that is similar to that observed with low doses of Taxol. Other possible applications for TPK1 inhibitors include therapy for non-insulin dependent diabetes (such as diabetes type II), obesity and alopecia.

Inhibitors of human TPK1 may also inhibit pfGSK3, an ortholog of this enzyme found in *Plasmodium falciparum*, as a consequence they could be used for the treatment of malaria (Biochimica et Biophysica Acta 1697, 181-196, 2004).

Recently, both human genetics and animal studies have pointed out the role of Wnt/LPR5 pathway as a major regulator of bone mass accrual.

Inhibition of TPK1 leads to the consequent activation of canonical Wnt signalling. Because deficient Wnt signalling has been implicated in disorders of reduced bone mass, TPK1 inhibitors may also be used for treating disorders of reduced bone mass, bone-related pathologies, osteoporosis.

According to recent data, TPK1 inhibitors might be used in the treatment or prevention of *Pemphigus vulgaris*.

Recent studies show that TPK1 inhibitor treatment improves neutrophil and megakaryocyte recovery. Therefore, TPK1 inhibitors will be useful for the treatment of neutropenia induced by cancer chemotherapy.

DISCLOSURE OF THE INVENTION

An object of the present invention is to provide compounds useful as an active ingredient of a medicament for preventive and/or therapeutic treatment of diseases such as Alzheimer disease. More specifically, the object is to provide novel compounds useful as an active ingredient of a medicament that enables radical prevention and/or treatment of the neurodegenerative diseases such as Alzheimer disease by inhibiting the TPK1 activity to suppress the neurotoxicity of A β and the formation of the PHF and by inhibiting the death of nerve cells.

In order to achieve the foregoing object, the inventors of the present invention conducted screenings of various compounds having inhibitory activity against the phosphorylation of TPK1. As a result, they found that compounds represented by the following formula (I) had the desired activity and were useful as an active ingredient of a medicament for preventive and/or therapeutic treatment of the aforementioned diseases. The present invention was achieved on the basis of these findings.

The present invention thus provides:

1. A compound represented by the formula (I), an optically active isomer thereof, or a pharmaceutically acceptable salt thereof.

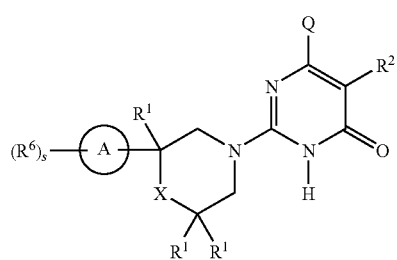

(I)

wherein each symbol is as defined below:

$R^1$ may be the same or different and represents hydrogen atom, a halogen atom, nitro group, cyano group, or a group represented by the following formula (I-f):

(I-f)

wherein $A^{14}$ represents hydrogen atom, a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ cycloalkenyl group which may be substituted,
a $C_6$-$C_{10}$ aryl group which may be substituted, a heterocyclic group which may be substituted,
$A^{13}$ represents bond, oxygen atom, sulfur atom or a group represented by the following formula (I-g):

(I-g)

wherein $A^{15}$ represents bond, C=O, C=S or S(=O)$_2$,
$A^{16}$ represents hydrogen atom, a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ cycloalkenyl group which may be substituted, a $C_6$-$C_{10}$ aryl group which may be substituted, or a heterocyclic group which may be substituted,
$A^{12}$ represents bond, C=O, C=S or S(=O)$_2$;

$A^{11}$ represents bond, oxygen atom, sulfur atom or a group represented by the following formula (I-h):

(I-h)

wherein $A^{17}$ represents bond, C=O, C=S or S(=O)$_2$;
$A^{18}$ represents hydrogen atom, a $C_1$-$C_6$ alkyl group which may be substituted, a $C_2$-$C_6$ group alkenyl which may be substituted, a $C_2$-$C_6$ alkynyl group which may be substituted, a $C_3$-$C_7$ cycloalkyl group which may be substituted, a $C_3$-$C_7$ cycloalkenyl group which may be substituted, a $C_6$-$C_{10}$ aryl group which may be substituted, or a heterocyclic group which may be substituted;
and $A^{14}$ and $A^{13}$, $A^{14}$ and $A^{11}$, $A^{13}$ and $A^{11}$ may combine to each other to form a heterocyclic ring,
X represents oxygen atom, sulfur atom, S=O, S(=O)$_2$, CH$_2$, CHR$^1$, CR$^1_2$, or a group represented by the following formula (I-e):

(I-e)

wherein $A^9$ represents bond, C=O, C=S or S(=O)$_2$,
$A^{10}$ represents hydrogen atom, a $C_1$-$C_6$ alkyl group which may be substituted, a $C_1$-$C_6$ alkyloxy group which may be substituted, a $C_2$-$C_6$ alkenyl group which may be substituted, a $C_2$-$C_6$ alkenyloxy group which may be substituted, a $C_2$-$C_6$ alkynyl group which may be substituted, a $C_3$-$C_7$ cycloalkyl group which may be substituted, a $C_3$-$C_7$ cycloalkyloxy group which may be substituted, a $C_3$-$C_7$ cycloalkenyl group which may be substituted, a $C_6$-$C_{10}$ aryl group which may be substituted, or a heterocyclic group which may be substituted;
A represents a $C_3$-$C_7$ cycloalkyl group, a $C_6$-$C_{10}$ aryl group or a heterocyclic group;
$R^6$ may be the same or different and represents a halogen atom, nitro group, cyano group, or a group represented by the following formula (I-k):

(I-k)

wherein $C^4$ represents hydrogen atom (except when all of $C^3$, $C^2$, and $C^1$ represent bond), a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ cycloalkenyl group which may be substituted, a $C_6$-$C_{10}$ aryl group which may be substituted, a heterocyclic group which may be substituted,
$C^3$ represents bond, oxygen atom, sulfur atom or a group represented by the following formula (I-l);

(I-l)

wherein $C^5$ represents bond, C=O, C=S or S(=O)$_2$, $C^6$ represents hydrogen atom, a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ cycloalkenyl group which may be substituted, a $C_6$-$C_{10}$ aryl group which may be substituted, or a heterocyclic group which may be substituted, $C^2$ represents bond, C=O, C=S or S(=O)$_2$, $C^1$ represents bond, oxygen atom, sulfur atom or a group represented by the following formula (I-m):

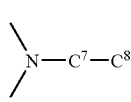

(I-m)

wherein $C^7$ represents bond, C=O, C=S or S(=O)$_2$, $C^8$ represents hydrogen atom, a $C_1$-$C_6$ alkyl which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ cycloalkenyl group which may be substituted, a $C_6$-$C_{10}$ aryl group which may be substituted, or a heterocyclic group which may be substituted, and $C^4$ and $C^3$, $C^4$ and $C^1$, $C^3$ and $C^1$ may combine to each other to form heterocyclic ring;

s represents 0 or an integer of 1 to 5;

Q represents a group represented by the following formula (II-a) or (II-b):

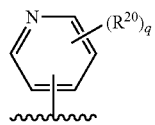

(II-a)

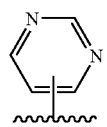

(II-b)

wherein $R^{20}$ may be the same or different and represents a halogen atom, nitro group, cyano group, or a group represented by the following formula (II-c):

$B^4$—$B^3$—$B^2$—$B^1$— (II-c)

wherein $B^4$ represents hydrogen atom (except when all of $B^3$, $B^2$, and $B^1$ represent bond), a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ cycloalkenyl group which may be substituted, a $C_6$-$C_{10}$ aryl group which may be substituted, a heterocyclic group which may be substituted, $B^3$ represents bond, oxygen atom, sulfur atom or a group represented by the following formula (II-d);

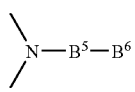

(II-d)

wherein $B^5$ represents bond, C=O, C=S or S(=O)$_2$, $B^6$ represents hydrogen atom, a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ cycloalkenyl group which may be substituted, a $C_6$-$C_{10}$ aryl group which may be substituted, or a heterocyclic group which may be substituted, $B^2$ represents bond, C=O, C=S or S(=O)$_2$, $B^1$ represents bond, oxygen atom, sulfur atom or a group represented by the following formula (II-e);

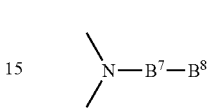

(II-e)

wherein $B^7$ represents bond, C=O, C=S or S(=O)$_2$, $B^8$ represents hydrogen atom, a $C_1$-$C_6$ alkyl group which may be substituted, a $C_2$-$C_6$ alkenyl group which may be substituted, a $C_2$-$C_6$ alkynyl group which may be substituted, a $C_3$-$C_7$ cycloalkyl group which may be substituted, a $C_3$-$C_7$ cycloalkenyl group which may be substituted, a $C_6$-$C_{10}$ aryl group which may be substituted, or a heterocyclic group which may be substituted, and $B^4$ and $B^3$, $B^4$ and $B^1$, $B^3$ and $B^1$ may combine to each other to form a heterocyclic ring, any two of $R^{20}$ may combine to each other to form an annulated carbocyclic or a heterocyclic ring, and q represents an integer of 1 to 4;

$R^2$ represents hydrogen atom, a halogen atom or a $C_1$-$C_6$ alkyl group which may be substituted.

2. The compound, an optically active isomer thereof, or a pharmaceutically acceptable salt thereof according to the above 1, wherein Q represents a group represented by the formula (II-a) wherein q represents 1 or 2.

3. The compound, an optically active isomer thereof, or a pharmaceutically acceptable salt thereof according to the above 1, wherein Q represents a group represented by the formula (II-b).

4. The compound, an optically active isomer thereof, or a pharmaceutically acceptable salt thereof according to any one of the above 1 to 3, wherein $R^2$ is hydrogen atom.

5. The compound, an optically active isomer thereof, or a pharmaceutically acceptable salt thereof according to any one of the above 1 to 4, wherein X represents oxygen atom.

6. The compound, an optically active isomer thereof, or a pharmaceutically acceptable salt thereof according to any one of the above 1 to 5, wherein each of $R^1$ is hydrogen atom, and A represents phenyl group.

7. The compound, an optically active isomer thereof, or a pharmaceutically acceptable salt thereof according to the above 6, wherein $R^6$ is selected from the group consisting of halogen atoms and s is 1.

8. The compound, an optically active isomer thereof, or a pharmaceutically acceptable salt thereof according to the above 6, wherein $R^6$ is selected from the formula (I-k), and $C^1$, $C^2$ and $C^3$ represents bond and $C^4$ represents a heterocyclic group which may be substituted.

9. The compound, an optically active isomer thereof, or a pharmaceutically acceptable salt thereof according to the above 8, wherein the heterocyclic group represented by $C^4$ is a 5 or 6 membered heteroaromatic ring which contains nitrogen and/or oxygen and which may be substituted.

10. The compound, an optically active isomer thereof, or a pharmaceutically acceptable salt thereof according to any one of the above 1 to 5, wherein each of $R^1$ is hydrogen atom, and A represents benzofuranyl group or benzoisoxazolyl group.

11. The compound, an optically active isomer thereof, or a pharmaceutically acceptable salt thereof according to any one of the above 1 to 5, wherein each of $R^1$ is hydrogen atom, and A represents a $C_3$-$C_7$ cycloalkyl group.

12. A compound according to the above 1 selected from the group consisting of:
2-((2-RS)-2-Cyclobutyl-morpholin-4-yl)-6-(3-fluoro-pyridin-4-yl)-3H-pyrimidin-4-one;
2-[(2S)-2-(4-Fluoro-phenyl)-morpholin-4-yl]-1H-[4,4']bipyrimidinyl-6-one;
2-[(2S)-2-(4-Fluoro-phenyl)-morpholin-4-yl]-6-(3-fluoropyridin-4-yl)-3H-pyrimidin-4-one; and
2-{(2S)-2-[4-(5-Methyl-[1,2,4]oxadiazol-3-yl)-phenyl]-morpholin-4-yl}-1H-[4,4']bipyrimidinyl-6-one;
an optically active isomer thereof, or a pharmaceutically acceptable salt thereof.

13. A medicament comprising as an active ingredient a substance selected from the group consisting of the compound represented by the formula (I) and an optically active isomer thereof, or a pharmaceutically acceptable salt thereof according to any one of the above 1 to 12.

14. The medicament according to the above 13 which is used for preventive and/or therapeutic treatment of a disease caused by abnormal tau protein kinase 1 activity.

15. The medicament according to the above 13 which is used for preventive and/or therapeutic treatment of a neurodegenerative disease.

16. The medicament according to the above 15, wherein the neurodegenerative disease is selected from the group consisting of Alzheimer's disease, Parkinson's disease, tauopathies, vascular dementia, acute stroke, traumatic injuries, cerebrovascular accidents, brain cord trauma, spinal cord trauma, peripheral neuropathies, retinopathies, and glaucoma.

17. The medicament according to the above 13 which is used for preventive and/or therapeutic treatment of non-insulin dependent diabetes, obesity, manic depressive illness, schizophrenia, alopecia, or cancers.

18. The medicament according to the above 17 wherein cancer is breast cancer, non-small cell lung carcinoma, thyroid cancer, T or B-cell leukaemia, or a virus-induced tumor.

19. The medicament according to the above 13 which is used for preventive and/or therapeutic treatment of malaria.

20. The medicament according to the above 13 which is used for preventive and/or therapeutic treatment of bone diseases.

21. The medicament according to the above 13 which is used for preventive and/or therapeutic treatment of *Pemphigus vulgaris*.

22. The medicament according to the above 13 which is used for preventive and/or therapeutic treatment of neutropenia induced by cancer chemotherapy.

MODE FOR CARRYING OUT THE INVENTION

Unless otherwise indicated, the following definitions are set forth to illustrate and defined the meaning and scope of the various terms used to describe the invention herein.

The term "$C_1$-$C_6$ alkyl" means alkyl having 1 to 6 carbon atoms which may be either linear or branched, for example, methyl, ethyl, n-propyl, isopropyl, n-butyl, isobutyl, sec-butyl, tert-butyl, n-pentyl, isopentyl, neopentyl, 1,1-dimethylpropyl, n-hexyl, isohexyl.

The term "$C_1$-$C_{12}$ alkyl" means alkyl having 1 to 12 carbon atoms which may be either linear or branched, for example, methyl, ethyl, n-propyl, isopropyl, n-butyl, isobutyl, sec-butyl, tert-butyl, n-pentyl, isopentyl, neopentyl, 1,1-dimethylpropyl, n-hexyl, isohexyl, heptyl, octyl, nonyl, decyl, undecyl or dodecyl.

The term "$C_2$-$C_6$ alkenyl" means alkenyl having 2 to 6 carbon atoms, for example, vinyl, propenyl, butenyl, pentenyl, hexenyl.

The term "$C_2$-$C_6$ alkynyl" means alkynyl group having 2 to 6 carbon atoms, for example, ethynyl, propynl, butynyl, pentynyl, hexynyl.

The term "$C_3$-$C_7$ cycloalkyl" means cycloalkyl having 3 to 7 atoms, for example, cyclopropyl, cyclobutyl, cyclopentyl, cyclohexyl, cycloheptyl.

The term "$C_6$-$C_{10}$ aryl" means a group having 6 to 10 carbon atoms derived from, for example, benzene, naphthalene, indane, indene, tetrahydronaphthalene. The bond position in the cycle is not limited.

The term "heterocyclic group", "heterocycle", and "heterocyclic ring" mean cyclic group derived from, for example, furan, dihydrofuran, tetrahydrofuran, pyran, dihydropyran, tetrahydropyran, benzofuran, dihydrobenzofuran, isobenzofuran, chromene, chroman, isochroman, thiophene, benzothiophene, pyrrole, pyrroline, pyrrolidine, imidazole, imidazoline, imidazolidine, pyrazole, pyrazoline, pyrazolidine, triazole, tetrazole, pyridine, pyridine oxide, piperidine, pyrazine, piperazine, pyrimidine, pyridazine, indole, indoline, isoindole, isoindoline, indazole, benzimidazole, benzotriazole, tetrahydroisoquinoline, benzothiazolinone, benzoxazolinone, purine, quinolizine, quinoline, phthalazine, naphthyridine, quinoxaline, quinazoline, cinnoline, pteridine, oxazole, oxazolidine, isoxazole, isoxazolidine, oxadiazole, thiazole, benzothiazole, thiazylidine, isothiazole, isothiazolidine, thiadiazole, benzodioxole, dioxane, benzodioxane, dithian, morpholine, thiomorpholine, phthalimide homopiperidinyl, homopiperazinyl. The bond position in the cycle is not limited.

In the specification, when a functional group is defined as "which may be substituted" or "optionally substituted", the number of substituents as well as their types and substituting positions are not particularly limited, and when two or more substituents are present, they may be the same or different. The substituent in the present specification means, for example, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, $C_6$-$C_{10}$ aryl, heterocycles, $C_1$-$C_6$ alkoxy, $C_3$-$C_6$ alkenyloxy, $C_3$-$C_6$ alkynyloxy, $C_3$-$C_7$ cycloalkyloxy, $C_3$-$C_7$ cycloalkenyloxy, $C_6$-$C_{10}$ aryloxy, heterocycleoxy, halogen (chlorine, bromine, fluorine, iodine), nitro, amino, cyano, hydroxyl, oxo, $C_1$-$C_6$ alkylcarbonyl, $C_2$-$C_6$ alkenylcarbonyl, $C_2$-$C_6$ alkynylcarbonyl, $C_3$-$C_7$ cycloalkylcarbonyl, $C_3$-$C_7$ cycloalkenylcarbonyl, $C_6$-$C_{10}$ arylcarbonyl, heterocyclecarbonyl, $C_1$-$C_6$ alkylsulfonyl, $C_2$-$C_6$ alkenylsulfonyl, $C_2$-$C_6$ alkynylsulfonyl, $C_3$-$C_7$ cycloalkylsulfonyl, $C_3$-$C_7$ cycloalkenylsulfonyl, $C_6$-$C_{10}$ arylsulfonyl, heterocyclesulfonyl, $C_1$-$C_6$ alkoxycarbonyl, $C_3$-$C_6$ alkenyloxycarbonyl, $C_3$-$C_6$ alkynyloxycarbonyl, $C_3$-$C_7$ cycloalkyloxycarbonyl, $C_3$-$C_7$ cycloalkenyloxycarbonyl, $C_6$-$C_{10}$ aryloxycarbonyl, heterocycleoxycarbonyl, amino, $C_1$-$C_6$ alkylamino, $C_3$-$C_6$ alkenylamino, $C_3$-$C_6$ alkynylamino, $C_3$-$C_7$ cycloalkylamino, $C_3$-$C_7$ cycloalkenylamino, $C_6$-$C_{10}$ arylamino, heterocycle-amino, N,N-di-$C_1$-$C_6$ alkylamino, aminocarbonyl, $C_1$-$C_6$ alkylaminocarbonyl, $C_3$-$C_6$ alkenylaminocarbonyl, $C_3$-$C_6$ alkynylaminocarbonyl, $C_3$-$C_7$ cycloalkylaminocarbonyl, $C_3$-$C_7$ cycloalkenylaminocarbonyl, $C_6$-$C_{10}$ arylaminocarbonyl, heterocycle-aminocarbonyl, N,N-di-$C_1$-$C_6$ dialkylaminocarbonyl. The number of substituents as well as their types and substituting positions are not particularly limited, and when two or more substituents are present, they may be the same or different. In the above substituents, every term expressed by "$C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, $C_6$-$C_{10}$ aryl, heterocycle or $C_1$-$C_6$ alkoxy" represents the same meaning as defined in the above. These substituents are also substituted by the substituents described above.

$R^2$ may preferably be hydrogen atom.

X may be preferably oxygen atom, $CH_2$, or a group represented by the formula (I-e) wherein $A^9$ represents bond and $A^{10}$ represents hydrogen atom. X may be more preferably oxygen atom. It is preferable that each of $R^1$ are hydrogen atom and A represents a $C_3$-$C_7$ cycloalkyl group, phenyl group, benzofuranyl group, or benzoisoxazolyl group and $R^6$ represents a halogen atom, or a group represented by the formula (I-k) wherein $C^4$ represents a $C_1$-$C_6$ alkyl group, $C^3$ represents bond or oxygen atom, $C^2$ represents bond or C=O, and $C^1$ represents bond or oxygen atom. The $C_3$-$C_7$ cycloalkyl group represented by A may preferably be cyclobutyl group. $R^6$ may be preferably a halogen atom, a heterocyclic group or a $C_1$-$C_6$ alkyoxy group, more preferably a halogen atom, furan, thiophene, pyrrole, imidazole, pyrazole, triazole, tetrazole, oxazole, isoxazole, oxadiazole, thiazole, isothiazole, thiadiazole. The symbol s may preferably be 0, 1 or 2.

$R^{20}$ may be preferably a halogen atom, a $C_1$-$C_3$ alkyl group, a $C_1$-$C_3$ alkyloxy group, or a $C_6$-$C_{10}$ aryl group, more preferably a halogen atom, methyl group, or phenyl group.

The symbol q may be preferably 1 or 2, more preferably 1.

The pharmaceutically acceptable salt of the compound represented by the aforementioned formula (I) may include the salt with inorganic acid such as hydrochloric acid, hydrobromic acid and the like and the salt with organic acid such as acetic acid, propionic acid, tartaric acid, fumaric acid, maleic acid, malic acid, oxalic acid, succinic acid, citric acid, benzoic acid and the like.

In addition to the compound represented by the aforementioned formula (I), an optically active isomer thereof, or a pharmaceutically acceptable salt thereof, their solvates and hydrates also fall within the scope of the present invention. The compound represented by the formula (I) may have one or more asymmetric carbon atoms. As for the stereochemistry of such asymmetric carbon atoms, they may independently be in either (R) and (S) configuration, and the pyrimidone derivative may exist as stereoisomers such as optical isomers, or diastereoisomers. Any stereoisomers of pure form, any mixtures of stereoisomers, racemates and the like fall within the scope of the present invention Examples of preferred compounds of the present invention are shown in the tables set out below. However, the scope of the present invention is not limited by the following compounds.

TABLE 1

| Compound No. | STRUCTURE |
|---|---|
| 1 | |
| 2 | 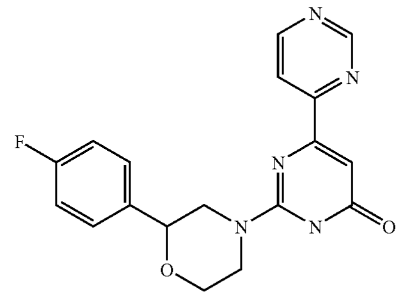 [SMILES: O=c1cc(-c2ccncn2)nc(N2CCOC(c3ccc(F)cc3)C2)[nH]1] |
| 3 | 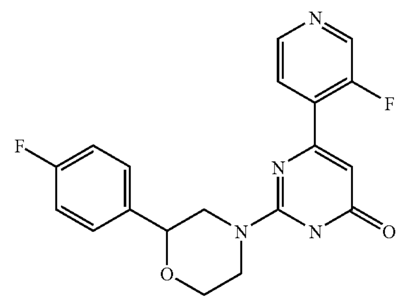 [SMILES: O=c1cc(-c2ccncc2F)nc(N2CCOC(c3ccc(F)cc3)C2)[nH]1] |
| 4 | 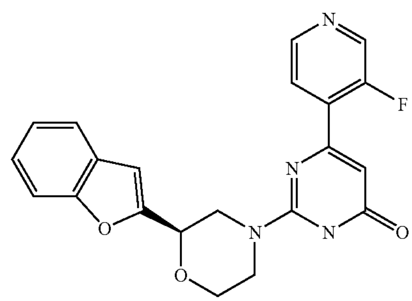 [SMILES: O=c1cc(-c2ccncc2F)nc(N2CCO[C@@H](c3cc4ccccc4o3)C2)[nH]1] |
| 5 | 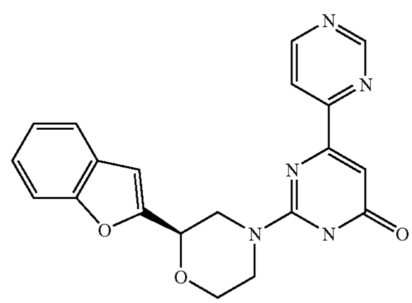 [SMILES: O=c1cc(-c2ccncn2)nc(N2CCO[C@@H](c3cc4ccccc4o3)C2)[nH]1] |
| 6 | 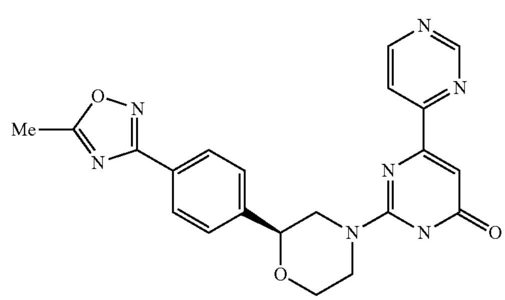 [SMILES: Cc1nc(-c2ccc([C@H]3CN(c4nc(-c5ccncn5)cc(=O)[nH]4)CCO3)cc2)no1] |

Particularly preferred compounds of the present invention represented by formula (I) include:

2-((2-RS)-2-Cyclobutyl-morpholin-4-yl)-6-(3-fluoro-pyridin-4-yl)-3H-pyrimidin-4-one;
2-[(2S)-2-(4-Fluoro-phenyl)-morpholin-4-yl]-1H-[4,4']bipyrimidinyl-6-one; and
2-[(2S)-2-(4-Fluoro-phenyl)-morpholin-4-yl]-6-(3-fluoro-pyridin-4-yl)-3H-pyrimidin-4-one; and
2-{(2S)-2-[4-(5-Methyl-[1,2,4]oxadiazol-3-yl)-phenyl]-morpholin-4-yl}-1H-[4,4']bipyrimidinyl-6-one
an optically active isomer thereof, or a pharmaceutically acceptable salt thereof.

Salts of the aforementioned preferred compound, and solvates or hydrates of the aforementioned compounds and salts thereof are also preferred.

The compounds represented by the aforementioned formula (I) can be prepared, for example, according to the method explained below.

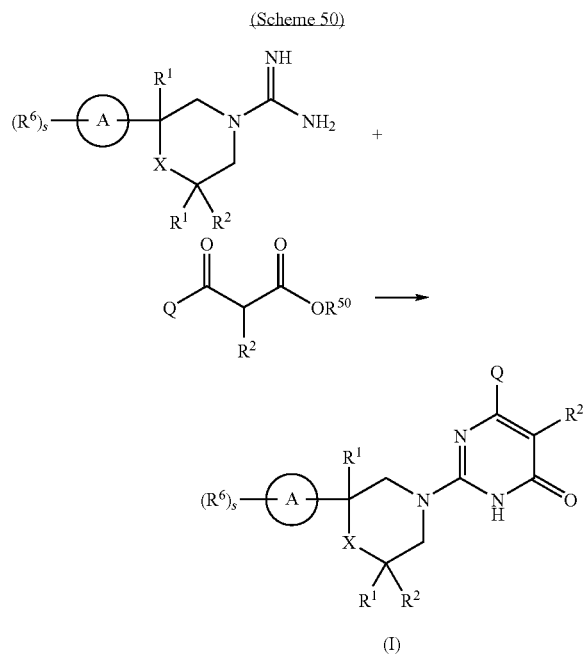

(In the above scheme, $R^{50}$ represents $C_1$-$C_6$ alkyl which may be substituted, $C_3$-$C_6$ alkenyl which may be substituted, $C_6$-$C_{10}$ aryl which may be substituted and $C_7$-$C_{12}$ aralkyl which may be substituted, and definitions of other symbol are the same as those already described.)

A compound represented by the formula (I) can be prepared, for example, by the condensation of corresponding 3-substituted 3-oxo-propionic acid ester and guanidine or salts thereof in the presence of a base such as sodium hydroxide, potassium hydroxide, sodium methoxide, sodium ethoxide, sodium carbonate, sodium hydrogencarbonate, potassium carbonate, triethylamine, diisopropylethylamine, N-methylpiperidine, N-ethylpiperidine, N-methylmorpholine and 1,8-diazabicyclo[5,4,0]undec-7-en for 1 to 300 hours at a suitable temperature ranging from 0° C. to 200° C. under nitrogen or argon atmosphere or under ordinary air to afford the desired compound (I').

Examples of a solvent for the reactions include, for example, alcoholic solvent such as methanol, ethanol, 1-propanol, isopropanol, tert-butanol, ethylene glycol, propylene glycol; etheric solvents such as diethyl ether, tert-butyl methyl ether, tetrahydrofuran, isopropyl ether; hydrocarbonic solvents such as benzene, toluene, xylene; halogenated hydrocarbonic solvents such as dichloromethane, chloroform, dichloroethane; aprotic polar solvents such as formamide, N,N-dimethylformamide, N,N-dimethylacetamide, N-methylpyrrolidone, dimethyl sulfoxide, sulfolane, hexamethylphosphoric triamide, water and the like. Generally, a single solvent or a mixture of two or more solvents may be used so as to be suitable to a base used.

The compounds of the present invention have inhibitory activity against TPK1, and they inhibit TPK1 activity in neurodegenerative diseases such as Alzheimer disease, thereby suppress the neurotoxicity of A β and the formation of PHF and inhibit the nerve cell death. Accordingly, the compounds of the present invention are useful as an active ingredient of a medicament which radically enables preventive and/or therapeutic treatment of Alzheimer disease. In addition, the compounds of the present invention are also useful as an active ingredient of a medicament for preventive and/or therapeutic treatment of ischemic cerebrovascular accidents, Down syndrome, cerebral bleeding due to solitary cerebral amyloid angiopathy, progressive supranuclear palsy, subacute sclerosing panencephalitis, postencephalitic parkinsonism, pugilistic encephalosis, Guam parkinsonism-dementia complex, Lewy body disease, Pick's disease, corticobasal degeneration frontotemporal dementia, vascular dementia, traumatic injuries, brain and spinal cord trauma, peripheral neuropathies, retinopathies and glaucoma, non-insulin dependent diabetes, obesity, manic depressive illness, schizophrenia, alopecia, breast cancer, non-small cell lung carcinoma, thyroid cancer, T or B-cell leukemia, and several virus-induced tumors. As the compound of the present invention has good safety and good pharmacokinetics, the compound has preferable characteristics as a medicament.

As the active ingredient of the medicament of the present invention, a substance may be used which is selected from the group consisting of the compound represented by the aforementioned formula (I) and pharmacologically acceptable salts thereof, and solvates thereof and hydrates thereof. The substance, per se, may be administered as the medicament of the present invention, however, it is desirable to administer the medicament in a form of a pharmaceutical composition which comprises the aforementioned substance as an active ingredient and one or more of pharmaceutical additives. As the active ingredient of the medicament of the present invention, two or more of the aforementioned substance may be used in combination.

A type of the pharmaceutical composition is not particularly limited, and the composition may be provided as any formulation for oral or parenteral administration. For example, the pharmaceutical composition may be formulated, for example, in the form of pharmaceutical compositions for oral administration such as granules, fine granules, powders, hard capsules, soft capsules, syrups, emulsions, suspensions, solutions and the like, or in the form of pharmaceutical compositions for parenteral administrations such as injections for intravenous, intramuscular, or subcutaneous administration, drip infusions, transdermal preparations, transmucosal preparations, nasal drops, inhalants, suppositories and the like.

Dose and frequency of administration of the medicament of the present invention are not particularly limited, and they may be appropriately chosen depending on conditions such as a purpose of preventive and/or therapeutic treatment, a type of a disease, the body weight or age of a patient, severity of a disease and the like. Generally, a daily dose for oral administration to an adult may be 0.01 to 1,000 mg (the weight of an active ingredient), and the dose may be administered once a day or several times a day as divided portions, or once in several days. When the medicament is used as an injection, administrations may preferably be performed continuously or intermittently in a daily dose of 0.001 to 3000 mg (the weight of an active ingredient) to an adult.

EXAMPLES

The present invention will be explained more specifically with reference to examples. However, the scope of the present invention is not limited to the following examples. The compound number in the examples corresponds to that in the table above.

Example 1

2-[(2S)-2-(4-Fluorophenyl)morpholin-4-yl]-1H-[4,4']bipyrimidinyl-6-one (Compound No. 2)

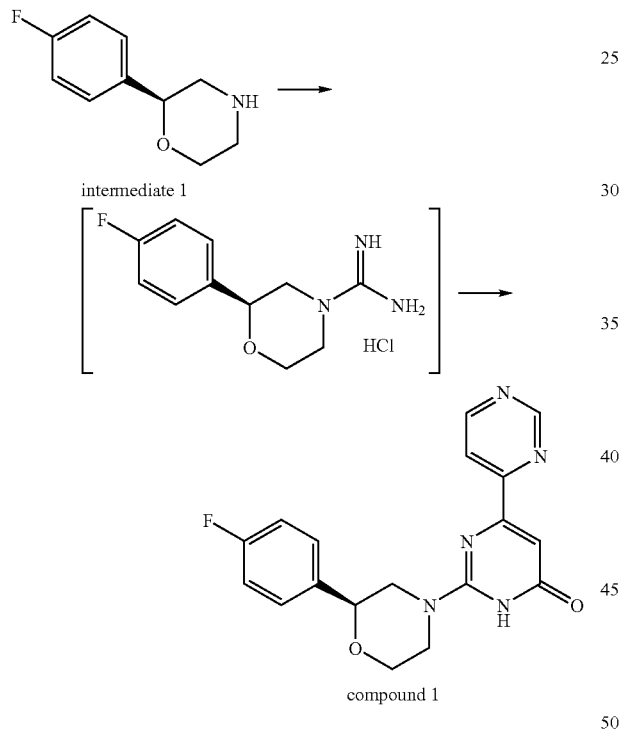

A solution of (2S)-2-(4-fluorophenyl)morpholine hydrochloride (intermediate 1, 2.1 g, 9.6 mmol), 1H-pyrazole-1-carboxamidine hydrochloride (2.8 g, 19.2 mmol), and diisopropylethylamine (6.5 g, 50.2 mmol) in methanol (25 ml) was stirred at room temperature for 12 hours. The solvent was evaporated off under reduced pressure and the crude (2S)-2-(4-fluorophenyl)morpholin-4-carboxamidine was afforded (7.47 g) as yellow oil. A solution of the carboxamidine (2.6 g), 3-oxo-3-pyrimidin-4-yl-propionic acid ethyl ester (0.98 g, 5.06 mmol), and potassium carbonate (1.4 g, 10.1 mmol) in ethanol (29 ml) was stirred at 80° C. for 18 hours. The solvent was removed under reduced pressure and the residue was partitioned between water and dichloromethane. The organic layer was dried over sodium sulfate and the solvent was removed under reduced pressure. The residue was purified by silica gel column chromatography (eluent; chloroform/methanol=10/1) to afford 2-[(2S)-2-(4-fluorophenyl)morpholin-4-yl]-1H-[4,4']bipyrimidinyl-6-one (Compound 1, 0.13 g) as yellow crystals.

Example 2

2-{(2S)-2-[4-(5-Methyl-[1,2,4]oxadiazol-3-yl)-phenyl]-morpholin-4-yl}-1H-[4,4']bipyrimidinyl-6-one (Compound No. 6)

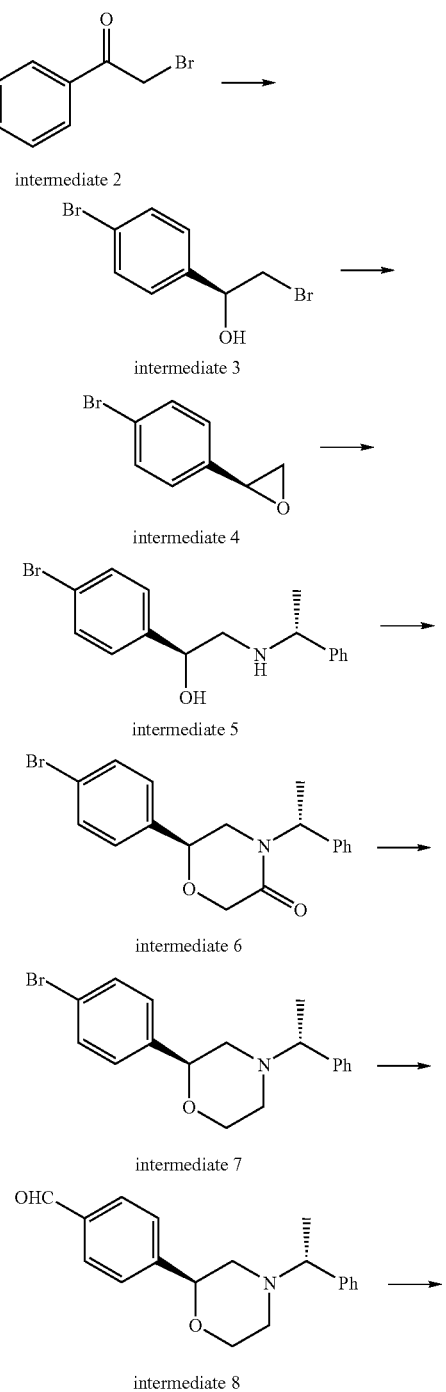

-continued

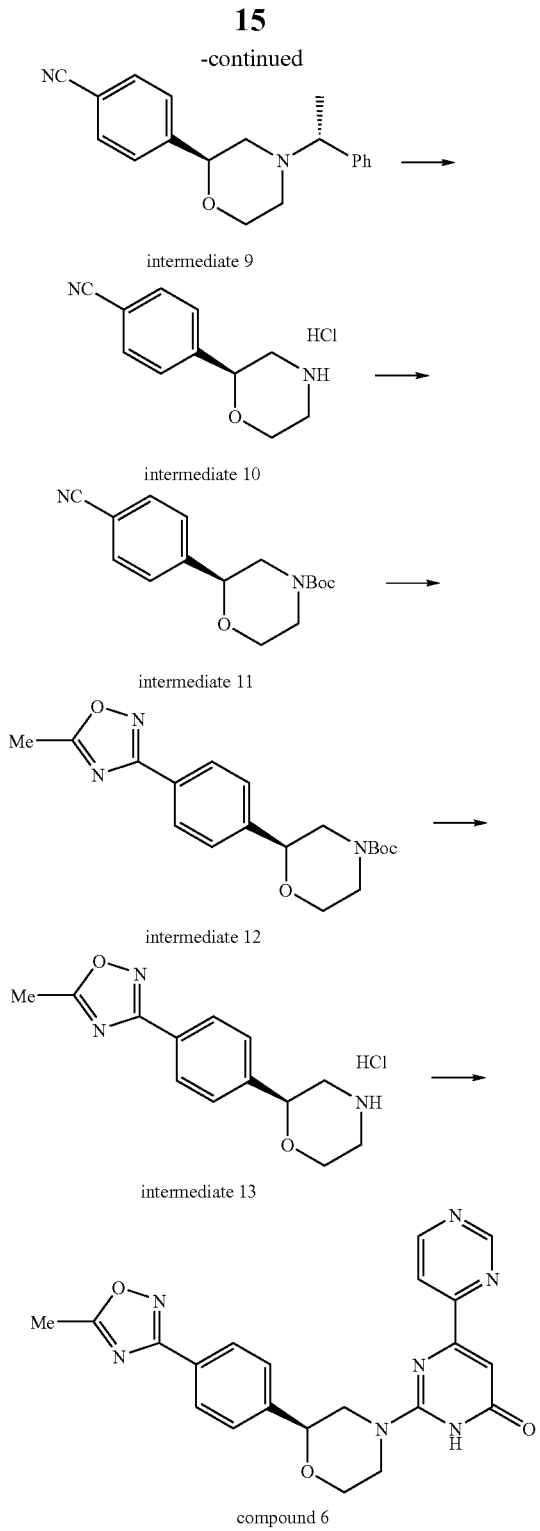

intermediate 9 intermediate 10 intermediate 11 intermediate 12 intermediate 13 compound 6

Example 2-1

2-Bromo-(1S)-1-(4-bromophenyl)ethanol (Intermediate 3)

(S)-CBS (25 ml, (S)-2-methyl-CBS-oxazaborolidine, manufactured by Aldrich, 1.0 M solution in toluene) was cooled to 0° C., and borane-tetrahydrofuran complex (185 ml, 185 mmol, 1.0 M solution in tetrahydrofuran) was added. After the flask was cooled by ice-sodium chloride bath, a solution of 4-bromophenacyl bromide (intermediate 2, 50.28 g, 181 mmol) in dichloromethane (300 ml) was added dropwise over one hour while maintaining the temperature at −5° C. to 0° C. After stirring the mixture at 0° C. for 50 minutes, methanol (12 ml) was added by small portions. Then, 0.5 M hydrochloric acid (300 ml) was added dropwise and the mixture was stirred at room temperature for 40 minutes. The precipitate was filtered off and the filtrate was partitioned between dichloromethane and water. The organic layer was separated and the aqueous layer was extracted with methylene chloride. The organic layers were combined, washed twice with 0.5 M hydrochloric acid and brine, and dried over anhydrous sodium sulfate. The solvent was evaporated under reduced pressure to afford 2-bromo-1-(1S)-(4-bromophenyl)ethanol (intermediate 3) as a pale-brown oil. This crude product was used for next step without purification.

Example 2-2

(2S)-2-(4-Bromophenyl)oxirane (Intermediate 4)

(2S)-2-Bromo-1-(4-bromophenyl)ethanol (intermediate 3) obtained above was dissolved in ethyl ether (300 ml), the solution was stirred with aqueous sodium hydroxide (14.47 g, 362 mmol in 300 ml of water) in a two-layer system at room temperature for 1.5 hours. The mixture was partitioned between diethyl ether and water, and the organic layer was washed with saturated brine and dried over anhydrous sodium sulfate. The solvent was evaporated under reduced pressure to give (2S)-2-(4-bromophenyl)oxirane (intermediate 4) as a pale-brown oil. This crude product was used for next step without purification.

$^1$H-NMR (300 MHz, CDCl$_3$) δ: 2.74-2.77(1H, m), 3.13-3.17(1H, m), 3.82-3.84(1H, m), 7.16(2H, d, J=8.4 Hz), 7.48(2H, d, J=8.4 Hz)

Example 2-3

(1S)-1-(4-Bromophenyl)-2-((1R)-1-phenylethylamino)ethanol (Intermediate 5)

A mixture of (2S)-2-(4-bromophenyl)oxirane (intermediate 4) obtained above and (R)-1-phenylethylamine (65.22 g, 538 mmol) was stirred in an oil bath with heating at 80° C. for 3 hours. Excess amine was distilled off under reduced pressure (ca. 70° C. at 7 mmHg). The resulting solid residue was cooled and then washed with isopropyl ether and dried to give (1S)-1-(4-bromophenyl)-2-((1R)-1-phenylethylamino) ethanol (intermediate 5, 46.76 g, 81% yield for 3 steps) as white crystals.

$^1$H-NMR (300 MHz, CDCl$_3$) δ: 1.39(3H, d, J=6.3 Hz), 2.48(1H, dd, J=9.0 Hz, 12.0 Hz), 2.77(1H, dd, J=3.6 Hz, 12.3 Hz), 3.82(1H, dd, J=6.6 Hz, 13.2 Hz), 7.16(2H, d, J=8.4 Hz), 7.20-7.27(3H, m), 7.31-7.34(2H, m), 7.41(2H, d, J=8.4 Hz)

MS: [M+H]$^+$=320

Melting point; 106.3° C.

Specific optical rotation; [α]$_D$=+80.74 (c=1.0, dichloromethane)

Example 2-4

(6S)-6-(4-Bromophenyl)-4-((1R)-1-phenylethyl)morpholin-3-one (Intermediate 6)

A solution of chloroacetyl chloride (19.5 ml, 245 mmol) in dichloromethane (100 ml) was added dropwise to a ice-cooled solution of (1S)-1-(4-bromophenyl)-2-((1R)-1-phenylethylamino)ethanol (intermediate 5, 71.0 g, 222 mmol) and triethylamine (34 ml, 245 mmol) in dichloromethane (600 ml). After the mixture was stirred for 2 hours, 1 M hydrochloric acid was added and the mixture was partitioned between water and chloroform. The organic layer was washed with saturated aqueous sodium hydrogen carbonate and brine, and dried over anhydrous sodium sulfate. The solvent was evaporated under reduced pressure and the residue was dissolved in 2-propanol (600 ml). The solution was added with potassium hydroxide (85%, 18.3 g, 278 mmol). The mixture was stirred at room temperature for 15 hours. The solvent was evaporated under reduced pressure and the residue was added with ethyl acetate. The mixture was partitioned between water and ethyl acetate, and the organic layer was washed with 1 M hydrochloric acid, saturated aqueous sodium hydrogen carbonate and brine, and dried over anhydrous magnesium sulfate. The solvent was evaporated under reduced pressure to give (6S)-6-(4-bromophenyl)-4-((1R)-1-phenylethyl)morpholin-3-one (intermediate 6, 92 g) as a brown oil. This crude product was used for next reaction without purification.

$^1$H-NMR (300 MHz, CDCl$_3$) δ: 1.53(3H, d, J=7.0 Hz), 2.96(1H, dd, J=3.0 Hz, 12.2 Hz), 3.29(1H, dd, J=10.8 Hz, 12.0 Hz), 4.38(1H, d, J=16.8 Hz), 4.49(1H, d, J=16.9 Hz), 4.53(1H, dd, J=3.0 Hz, 10.6 Hz), 6.53(1H, q, J=7.2 Hz), 7.14(2H, d, J=8.3 Hz), 7.28-7.39(5H, m), 7.45(2H, d, J=8.4 Hz)

MS: [M+H]$^+$=360

Specific optical rotation; [α]$_D$=+71.68 (c=0.5, chloroform)

Example 2-5

(2S)-2-(4-Bromophenyl)-4-((1R)-1-phenylethyl)morpholine (Intermediate 7)

To a ice-cooled solution of (6S)-6-(4-bromophenyl)-4-((1R)-1-phenylethyl) morpholin-3-one (intermediate 6, 92 g) obtained in step 1-10 in tetrahydrofuran (400 ml) was added dropwise over 30 minutes a borane-tetrahydrofuran complex (1.0 M solution in tetrahydrofuran, 600 ml, 600 mmol). After being warmed to room temperature and stirred for 2 hours, the mixture was ice-cooled again and added dropwise with methanol (70 ml). The solvent was evaporated under reduced pressure. The residue was added with methanol (750 ml) and 1 M aqueous sodium hydroxide (280 ml). The mixture was stirred at 80° C. for one hour, during which period 1 M aqueous sodium hydroxide (70 ml) was added 3 times in every 15 minutes. After the mixture was cooled to room temperature, methanol was evaporated under reduced pressure and the resulting solution was extracted with ethyl acetate. The organic layers was washed with water and brine, and dried over anhydrous sodium sulfate. The solvent was evaporated under reduced pressure to give (2S)-2-(4-bromophenyl)-4-((1R)-1-phenylethyl)morpholine (intermediate 7, 68 g, yield 88% from intermediate 5) as white crystals.

IR(ATR): 1487, 1449, 1117, 1098, 809, 758, 699, 550 cm$^{-1}$ $^1$H-NMR (CDCl$_3$) δ: 1.35(3H, d), 2.10(2H, m), 2.60(1H, m), 3.05(1H, m), 3.35(1H, q), 3.75(1H, m), 3.89(1H, m), 4.55(1H, m), 7.25(7H, m), 7.46(2H, d)

MS: [M+H]$^+$=346

Melting point; 88.0° C.

Specific optical rotation; [α]$_D$=+32.06 (c=1.0, dichloromethane)

Example 2-6

4-((2S)-4-((1R)-1-Phenylethyl)morpholin-2-yl)benzaldehyde (Intermediate 8)

To a solution of (2S)-2-(4-bromophenyl)-4-((1R)-1-phenylethyl)morpholine (intermediate 7, 63.3 g, 183 mmol) in tetrahydrofuran (450 ml) was added n-butyllithium (1.57 M in hexane solution, 175 ml, 275 mmol) at −78° C. and the mixture was stirred for 20 minutes. N,N-dimethylformamide (28.3 ml 365 mmol) was added and the mixture was stirred for 2 hours at −78° C. and then allowed to be warmed to −10° C. The reaction was quenched with aqueous ammonium chloride, and the resulting solution was partitioned between water and ethyl acetate. The organic layer was washed with water and brine and dried over sodium sulfate. The solvent was evaporated under reduced pressure to afford crude 4-((2S)-4-((1R)-1-phenylethyl) morpholin-2-yl)benzaldehyde (intermediate 8, 55.1 g). This compound was used without further purification.

Example 2-7

4-((2S)-4-((1R)-1-Phenylethyl)morpholin-2-yl)benzonitrile (Intermediate 9)

To a solution of crude 4-((2S)-4-((1R)-1-phenylethyl)morpholin-2-yl) benzaldehyde (intermediate 8, 55.1 g) in ethanol (280 ml) was added sodium acetate (30.0 g, 365 mmol) and hydroxylamine hydrochloride (25.4 g, 365 mmol) at room temperature. After a reflux for 2 hours, the mixture was partitioned between water and dichloromethane, and the organic layer was washed with water and brine and dried over sodium sulfate. The solvent was evaporated under reduced pressure. The residue was then added with acetic acid (140 ml) and acetic anhydride (140 ml). After the mixture was refluxed for 2 hours, the solvent was removed under reduced pressure. The residue was partitioned between water and chloroform. The organic layer was washed with aqueous sodium hydrogen carbonate, dried over sodium sulfate, and the solvent was removed under reduced pressure. The residue was purified by silica gel column chromatography (eluent; hexane/ethyl acetate=9/1) to afford 4-((2S)-4-((1R)-1-phenylethyl)morpholin-2-yl)benzonitrile (intermediate 9, 45.7 g, 86% from intermediate 7)

$^1$H NMR (400 MHz, CDCl$_3$) δ: 1.37 (3H, d, J=7.0 Hz), 2.01 (1H, t, J=11.0 Hz), 2.15 (1H, dt, J=3.1, 11.7 Hz), 2.60-2.65 (1H, m), 3.08-3.12 (1H, m), 3.39 (1H, q, J=7.0 Hz), 3.74 (1H, dt, J=2.4, 11.7 Hz), 3.92-3.96 (1H, m), 4.65 (1H, dd, J=2.4, 10.2), 7.24-7.35 (5H, m), 7.48 (2H, d, J=7.8 Hz), 7.63 (2H, d, J=7.8 Hz)

MS: [M+H]$^+$=293

Melting point; 83.6° C.

Specific optical rotation; [α]$_D$=+46.23 (c=0.5, chloroform)

Example 2-8

4-((2S)-Morpholin-2-yl)benzonitrile hydrochloride (Intermediate 10)

To a solution of 4-((2S)-4-((1R)-1-phenylethyl)morpholin-2-yl)benzonitrile (intermediate 9, 45.7 g, 156 mmol) in 1,2-dichloroethane (312 ml) was added 1-chloroethyl chloroformate (66.9 g, 468 mmol) at room temperature. After a reflux for 6 hours, the solution was concentrated under reduced pressure. The residue was dissolved in methanol (312 ml) and the solution was refluxed for 2 hours. After removal of the solvent under reduced pressure, the crude product was washed with acetone and dried under reduced pressure to afford 4-((2S)-morpholin-2-yl)benzonitrile hydrochloride (intermediate 10, 27.6 g, 79%).

$^1$H NMR (400 MHz, DMSO-d$_6$) δ: 2.99 (1H, t, J=11.7 Hz), 3.12 (1H, dt, J=3.1, 12.5 Hz), 3.25-3.28 (1H, m), 3.48-3.52 (1H, m), 3.92 (1H, dt, J=2.4, 11.7 Hz), 4.15 (1H, dd, J=3.1, 12.5 Hz), 4.86 (1H, dd, J=2.4, 11.7 Hz), 7.60 (2H, d, J=8.6 Hz), 7.90 (2H, d, J=8.6 Hz), 9.37 (2H, brs)

MS: [M+H]$^+$=189
Melting point; 195.8° C.
Specific optical rotation; [α]$_D$=+30.39 (c=0.5, methanol)

Example 2-9 tert-Butyl (2S)-2-(4-cyanophenyl)morpholine-4-carboxylate (Intermediate 11)

To a solution of 4-((2S)-morpholin-2-yl)benzonitrile hydrochloride (intermediate 10, 17.9 g, 79.8 mmol) in tetrahydrofuran (400 ml) was added triethylamine (24.2 g, 240 mmol) and di-tert-butyl dicarbonate (19.2 g, 87.8 mmol) at 0° C. and the mixture was stirred at room temperature for 3 hours. The resulting solution was partitioned between water and ethyl acetate, and the organic layer was washed with brine, dried over sodium sulfate, and the solvent was removed under reduced pressure. The residue was purified by silica gel column chromatography (eluent; hexane/ethyl acetate=6/1) to afford tert-butyl (2S)-2-(4-cyanophenyl)morpholine-4-carboxylate (intermediate 11, 17.6 g, 77%)

$^1$H NMR (400 MHz, CDCl$_3$) δ: 1.49 (9H, s), 2.69-2.80 (1H, m), 3.00-3.09 (1H, m), 3.65-3.72 (1H, m), 3.90-4.23 (3H, m), 4.48 (1H, d, J=11.0 Hz), 7.50 (2H, d, J=7.8 Hz), 7.66 (2H, d, J=7.8 Hz)

MS: [M+H]$^+$=289
Melting point; 104.2° C.
Specific optical rotation; [α]$_D$=−37.35 (c=0.5, chloroform)

Example 2-10 tert-Butyl (2S)-2-(4-(5-methyl-1,2,4-oxadiazol-3-yl)phenyl)morpholine-4-carboxylate (intermediate 12)

To a solution of tert-butyl (2S)-2-(4-cyanophenyl)morpholine-4-carboxylate (intermediate 11, 17.6 g, 61.1 mmol) and hydroxylamine hydrochloride (12.8 g, 183 mmol) in ethanol (120 ml) was added sodium carbonate (32.4 g, 305 mmol) in water (120 ml) at room temperature and the mixture was stirred at 80° C. for 3 hours. After removal of the solvent under reduced pressure, the residue was partitioned between water and ethyl acetate. The organic layer was washed with brine and dried over sodium sulfate. The solvent was evaporated under reduced pressure. The residue was added with xylene (150 ml) and N,N-dimethylacetamide dimethylacetal (18.1 g, 122 mmol). After the solution was refluxed for 2 hours, water was azeotropically removed using a Dean-Stark water separator with molecular sieves 4A. The mixture was concentrated under reduced pressure, and the residue was purified by silica gel column chromatography (eluent; hexane/ethyl acetate=3/1) to afford tert-butyl (2S)-2-(4-(5-methyl-1,2,4-oxadiazol-3-yl)phenyl)morpholine-4-carboxylate (intermediate 12, 16.9 g, 80%)

$^1$H NMR (400 MHz, CDCl$_3$) δ: 1.49 (9H, s), 2.66 (3H, s), 2.77-2.90 (1H, m), 3.02-3.11 (1H, m), 3.67-3.74 (1H, m), 3.89-4.25 (3H, m), 4.48 (1H, d, J=11.0 Hz), 7.50 (2H, d, J=7.8 Hz), 8.00 (2H, d, J=7.8 Hz)

MS: [M+H]$^+$=246 (-tert-BuOCO)
Melting point; 114.4° C.
Specific optical rotation; [α]$_D$=−34.93 (c=0.5, chloroform)

Example 2-11

(2S)-2-(4-(5-Methyl-1,2,4-oxadiazol-3-yl)phenyl)morpholine hydrochloride (intermediate 13)

To a solution of tert-butyl (2S)-2-(4-(5-methyl-1,2,4-oxadiazol-3-yl)phenyl)morpholine-4-carboxylate (intermediate 12, 16.9 g, 49.0 mmol) in ethyl acetate (60 ml) was added 4N hydrogen chloride in ethyl acetate (150 ml) at room temperature and the solution was stirred for 3 hours. The solvent was evaporated under reduced pressure, and the resulting precipitate was filtered, washed with ethyl acetate, and dried under reduced pressure to afford (2S)-2-(4-(5-methyl-1,2,4-oxadiazol-3-yl) phenyl)morpholine hydrochloride (intermediate 13, 13.3 g, 96%).

$^1$H NMR (400 MHz, DMSO-d$_6$) δ: 2.67 (3H, s), 3.00 (1H, t, J=12.5 Hz), 3.12 (1H, dt, J=3.9 12.5 Hz), 3.27 (1H, d, J=12.5 Hz), 3.48 (1H, d, J=12.5 Hz), 3.97 (1H, dt, J=2.4, 12.5 Hz), 4.15 (1H, dd, J=3.1, 12.5 Hz), 4.89 (1H, dd, J=1.6, 11.0 Hz), 7.58 (2H, d, J=8.6 Hz), 8.03 (2H, d, J=8.6 Hz), 9.62 (2H, brs)

MS: [M+H]$^+$=246
Melting point; 286.8° C.
Specific optical rotation; [α]$_D$=+29.98 (c=0.5, methanol)

Example 2-12

2-{(2S)-2-[4-(5-Methyl-[1,2,4]oxadiazol-3-yl)-phenyl]-morpholin-4-yl}-1H-[4,4']bipyrimidinyl-6-one (Compound 6)

To a solution of (2S)-2-(4-(5-methyl-1,2,4-oxadiazol-3-yl)phenyl)morpholine hydrochloride (intermediate 13, 4.00 g, 14.2 mmol) and 1H-pyrazole-1-carboxamidine hydrochloride (2.19 g, 14.9 mmol) in N,N-dimethylformamide (14 ml) was added. N,N-diisopropylethylamine (4.05 g, 31.3 mmol) at room temperature and the solution was stirred for 4 hours. The solution was decanted with ether, then 3-oxo-3-pyrimidin-4-yl-propionic acid ethyl ester (3.59 g, 18.5 mmol), potassium carbonate (4.92 g, 35.6 mmol) and ethanol (30 ml) were added to the resulting solution. After refluxed for 18 hours, the solution was concentrated under reduced pressure. The residue was washed with water and the hot mixture of ethanol and 1N hydrochloric acid (1/1, v/v), and dried under reduced pressure to afford 2-{(2S)-2-[4-(5-methyl-[1,2,4]oxadiazol-3-yl)-phenyl]-morpholin-4-yl}-1H-[4,4']bipyrimidinyl-6-one (1.94 g, 33%).

The compounds in the following table were prepared in the same manner as the methods described above. The compound numbers in the following table correspond to those shown in the above-described table of preferred compounds.

TABLE 2

| Compound No. | $^1$H-NMR | LC-MS (M + 1) |
|---|---|---|
| 1 | 1.88-1.97 (6H, m), 2.20-2.26 (1H, m), 2.56-2.60 (1H, m), 2.92-3.02 (1H, m), 3.33-3.36 (1H, m), 3.48-3.52 (1H, m), 3.88-3.94 (1H, m), 4.27-4.33 (2H, m), 6.25 (1H, s), 7.96 (1H, dd, J = 1.2 Hz, 4.2 Hz), 8.55 (1H, d, J = 4.2 Hz), 8.68 (1H, d, J = 1.2 Hz), 11.66 (1H, br) (CDCl$_3$). | 331 |
| 2 | 3.03 (1H, dd, J = 13.2 Hz and 10.5 Hz), 3.30 (1H, m), 3.87 (1H, td, J = 11.7 Hz and 2.4 Hz), 4.25 (1H, dd, J = 11.7 Hz and 2.7 Hz), 4.58-4.66 (2H, m), | 354 |

TABLE 2-continued

| Compound No. | $^1$H-NMR | LC-MS (M + 1) |
|---|---|---|
|  | 4.74 (1H, d, J = 13.2 Hz), 7.01 (1H, s), 7.16 (2H, t, J = 8.7 Hz), 7.52-7.57 (2H, m), 8.14 (1H, d, J = 1.2 Hz and 5.1 Hz), 8.88 (1H, d, J = 5.1 Hz), 9.31 (1H, d, J = 1.2 Hz), 12.44 (1H, br.s) (CDCl$_3$). |  |
| 3 | 3.04 (1H, dd, J = 13.2 Hz and 10.5 Hz), 3.28 (1H, m), 3.88 (1H, td, J = 11.7 Hz and 2.4 Hz), 4.20 (1H, dd, J = 11.7 Hz and 2.7 Hz), 4.40 (1H, d, J = 13.3 Hz), 4.50 (1H, d, J = 13.5 Hz), 4.80 (1H, d, J = 10.6 Hz), 6.48 (1H, s), 7.10 (1H, td, J = 8.5 Hz and 2.2 Hz), 7.36-7.48 (3H, m), 7.95 (1H, dd, J = 6.4 Hz and 5.3 Hz), 8.46 (1H, d, J = 5.1 Hz), 8.52 (1H, d, J = 3.0 Hz) (CDCl$_3$). | 371 |
| 4 | 3.26-3.35 (1H, m), 3.47 (1H, dd, J = 10.0, 13.2 Hz), 3.75 (1H, dt, J = 2.5, 11.2 Hz), 4.02 (1H, d, J = 11.6 Hz), 4.37 (1H, d, J = 13.0 Hz), 4.66 (1H, d, J = 13.6 hz), 4.83 (1H, d, J = 3.1, 9.8 Hz), 6.35 (1H, s), 6.96 (1H, s), 7.24-7.35 (2H, m), 7.59 (1H, d, J = 8.1 Hz), 7.64-7.67 (1H, m), 7.99 (1H, dd, J = 5.1, 6.7 Hz), 8.54 (1H, d, J = 4.4 Hz), 8.68 (1H, d, J = 3.1 Hz), 11.73 (1H, s) (DMSO-d6) | 393 |
| 5 | 3.26-3.77 (1H, m), 3.49 (1H, dd, J = 10.2, 12.6 Hz), 3.76 (1H, t, J = 11.0 Hz), 4.03 (1H, d, J = 11.5 Hz), 4.35-4.48 (1H, m), 4.63-4.77 (1H, m), 4.84 (1H, d, J = 9.8 Hz), 6.69-6.90 (1H, m), 6.98 (1H, s), 7.24-7.36 (2H, m), 7.60 (1H, d, J = 8.2 Hz), 7.66 (1H, d, J = 7.6 Hz), 8.28 (1H, d, J = 4.5 Hz), 8.96 (1H, d, J = 5.2 Hz), 9.29 (1H, s), 11.75 (1H, s) (DMSO-d6) | 376 |
| 6 | 2.68 (3H, s), 3.08 (1H, dd, J = 11.0, 13.3 Hz), 3.33 (1H, dt, J = 3.1, 12.5 Hz), 3.90 (1H, dt, J = 2.4, 11.7 Hz), 4.28 (1H, dd, J = 2.4, 11.7 Hz), 4.61 (1H, d, J = 13.3 Hz), 4.72 (1H, dd, J = 2.4, 11.0 Hz), 4.80 (1H, d, J = 13.3 Hz), 7.07 (1H, s), 7.69 (2H, d, J = 7.8 Hz), 8.15 (1H, dd, J = 1.6, 5.5 Hz), 8.18 (2H, d, J = 7.8 Hz), 8.89 (1H, d, J = 4.7 Hz), 9.35 (1H, d, J = 1.6 Hz), 12.33-12.66 (1H, brs) (CDCl$_3$) | 418 |

EXPERIMENT 1

Inhibitory Activity of the Medicament of the Present Invention Against P-GS1 Phosphorylation by Bovine Cerebral TPK1

A mixture containing 100 mM MES-sodium hydroxide (pH 6.5), 1 mM magnesium acetate, 0.5 mM EGTA, 5 mM β-mercaptoethanol, 0.02% Tween 20, 10% glycerol, 12 μg/ml P-GS1, 41.7 μM [γ-$^{32}$P] ATP (68 kBq/ml), bovine cerebral TPK1 and a compound shown in Table (a final mixture contained 1.7% DMSO deriving from a solution of a test compound prepared in the presence of 10% DMSO) was used as a reaction system. The phosphorylation was started by adding ATP, and the reaction was conducted at 25° C. for 2 hours, and then stopped by adding 21% perchloric acid on ice cooling. The reaction mixture was centrifuged at 12,000 rpm for 5 minutes and adsorbed on P81 paper (Whatmann), and then the paper was washed four times with 75 mM phosphoric acid, three times with water and once with acetone. The paper was dried, and the residual radioactivity was measured using a liquid scintillation counter. The results are shown in the table below. The test compound markedly inhibited the P-GS1 phosphorylation by TPK1. The results strongly suggest that the medicaments of the present invention inhibit the TPK1 activity, thereby suppress the Aβ neurotoxicity and the PHF formation, and that the medicaments of the present invention are effective for preventive and/or therapeutic treatment of Alzheimer disease and the above-mentioned diseases.

TABLE 3

| Compound No. | IC$_{50}$ (nM) |
|---|---|
| 2 | 86.3 |
| 3 | 59.8 |

EXPERIMENT 2

Inhibitory Activity on Tau Phosphorylation In Vivo

Test compound was administered to male CD-1 mice of 5-6 weeks weighing 25-35 g (Charles River Japan, inc.) at 1, 3, 10, 30 mg/kg p.o. (0.5% Tween/H$_2$O suspension) and after 1 h, mice were decapitated and cortex was promptly removed, followed by being frozen in liquid N$_2$. Cortex was directly homogenized with 2.3% SDS homogenization buffer (62.5 mM Tris-HCl, 2.3% SDS, 1 mM each of EDTA, EGTA and DTT, protease inhibitor cocktail (sigma P2714) containing 0.2 μM 4-(2-Aminoethyl)benzenesulfonyl fluoride (AEBSF), 13 μM bestatin, 1.4 μM E-64, 0.1 mM leupeptin, 30 nM aprotinin, pH 6.8) and centrifuged at 15000×g for 15 min at 4° C. Protein concentrations were determined using DC protein assay kit (BIO-RAD). Supernatants were diluted with sample buffer (62.5 mM Tris-HCl, 25% glycerol, 2% SDS, 0.01% Bromophenol Blue, pH6.8) to adjust the protein concentrations around 0.5-2 mg/mg and then boiled for 5 min. 10 μg of samples were applied on 10% SDS-PAGE mini slab gels and transferred onto PVDF membranes. Membranes were incubated with PBS containing 5% non-fat milk for 1 h at r.t. and then probed with pS396 anti-body (BIOSOURCE) over night at 4° C. Anti-rabbit IgG HRP-conjugated anti-body (Promega) was used as secondary anti-body. Membranes were visualized by ECL kit (Amerasham Bioscience) and detected by LAS1000 (Fuji Photo Film).

Solubility Example (1). Preparation 1-1. JP-1 Fluid

To 2.0 g of sodium chloride, 7.0 mL of hydrochloric acid and water were added and the solution was adjusted to 1000 mL. This solution was clear and colorless, with pH of approximately 1.2.

1-2. JP-2 Fluid

To 250 mL of 0.2 mol/L potassium dihydrogen phosphate test solution, 118 mL of 0.2 mol/L sodium hydroxide test solution and water were added and the solution was adjusted to 1000 mL. This solution was clear and colorless, with pH of approximately 6.8.

1-3. Diluted McIlvaine Buffer (pH 4.0)

Disodium hydrogen phosphate solution (0.05 mol/L) and 0.0025 mol/L citric acid solution were mixed and the mixture was adjusted to pH4.0 to prepare a diluted McIlvaine buffer.

3-4. Artificial Intestinal Solutions

Two artificial intestinal fluid formulations were used: fasted-state simulated intestinal fluid (FaSSIF) and fed-state simulated intestinal fluid (FeSSIF)(Pharm. Res., Vol. 15, No. 5, 1998, p 698-705). In order to prepare these solutions, the test reagents were combined as shown in Table 4, the mixture was added with water, and the preparations were homogenized by supersonic vibration. After confirming that the emulsifications were homogeneous, the pH was adjusted by adding 1 mol/L sodium hydroxide solution and the volume of solution was adjusted by adding appropriate amount of water.

TABLE 4

Compositions of simulated intestinal fluid

| FaSSIF | | FeSSIF | |
|---|---|---|---|
| PH | 6.5 | pH | 5 |
| Osmolality | 270 mOsmol | Osmolality | 635 mOsmol |
| Sodium taurocholate | 3 mM | Sodium taurocholate | 15 mM |
| Lecithin | 0.75 mM | Lecithin | 3.75 mM |
| KH2PO4 | 3.9 g | Acetic acid | 8.65 g |
| KCl | 7.7 g | KCl | 15.2 g |
| NaOH | pH 6.5 | NaOH | pH 5.0 |
| Water | 1 L | Water | 1 L |

(2) Determination of the Appropriate Quantitative Measurement Method

For the purpose of rapid qualitative measurement, the rapid analysis method (conditions described in more detail below) using semi-micro columns was developed to produce evenly symmetrical, discrete test compounds peaks separated from solvent shock peaks.

[HPLC Conditions]
Detector: Photodiode array
Wavelength: UV235 nm
Column: inertsil ODS-3 5 μm 3.0 mm I.D.×75 mm
Column temperature: 40° C.
Mobile phase: A, 0.1% trifluoroacetic acid solution
B, 0.1% trifluoroacetic acid/acetonitrile solution
A:B=65:35 (isocratic elution)
Flow rate: 0.50 mL/min
Injection volume: 5 μL (3) Determination of the Appropriate Solubility Measurement Method After the potential of test material to be adsorbed on various type of filters was examined, solubility measurements were conducted by removing insoluble components by filtration.

(4) Measurement Procedures of Sample Solubility to JP-14 First Fluid, JP-14 Second Fluid, McIlvaine Buffer (pH=4.0), Water, and Artificial Intestinal Fluids (Fasted-State and Fed-State)

The test liquid (70 mL) was added to a 200 mL conical flask which was warmed to 37° C. in water bath. Approximately 70 mg of each test material was directly added to the flask, dispersed by supersonic vibration for 5 minutes, then stirred at approximately 600 rpm (confirmed by tachometer readings) using a magnetic stir rod of approximately 5 cm long. At the pre-determined sampling times after the solubility measurement started, 5 mL of the test solution was taken and filtered through the membrane filter (DISMIC-25HP) having a pore size of 0.45 μm or less. 500 μL of the filtered solution was precisely measured after the initial 2.0 mL was discarded. Acetonitrile of 500 μL was precisely measured and added to this filtered solution to make a test solution for HPLC.

Separately, approximately 5 mg of the test compound was weighed precisely and the solvent such as acetonitrile or 50% acetonitrile/water solution was added to make a standard solution in a concentration of approximately 50 μg/mL. Peak areas of $A_T$ and As were measured by the liquid chromatography under the conditions above-mentioned for 5 μL aliquots of the test solution and the standard solution, respectively, and, from which the solubility of test materials was determined using a one-point standard calibration method.

Formulation Example (1) Tablets

The ingredients below were mixed by an ordinary method and compressed by using a conventional apparatus.

| Compound of Example 1 | 30 mg |
|---|---|
| Crystalline cellulose | 60 mg |
| Corn starch | 100 mg |
| Lactose | 200 mg |
| Magnesium stearate | 4 mg |

(2) Soft Capsules

The ingredients below were mixed by an ordinary method and filled in soft capsules.

| Compound of Example 1 | 30 mg |
|---|---|
| Olive oil | 300 mg |
| Lecithin | 20 mg |

Industrial Applicability

The compounds of the present invention have TPK1 inhibitory activity and are useful as an active ingredient of a medicament for preventive and/or therapeutic treatment of diseases caused by abnormal advance of TPK1 such as neurodegenerative diseases (e.g. Alzheimer disease) and the above-mentioned diseases.

The invention claimed is:
1. 2-{(2S)-2-[4-(5-Methyl-[1,2,4]oxadiazol-3-yl)-phenyl]-morpholin-4-yl}-1H-[4,4']bipyrimidinyl-6-one, an optically active isomer thereof, or a pharmaceutically acceptable salt thereof.
2. A medicament composition comprising as an active ingredient 2-{(2S)-2-[4-(5-Methyl-[1,2,4]oxadiazol-3-yl)-phenyl]-morpholin-4-yl}-1H-[4,4']bipyrimidinyl-6-one, an optically active isomer thereof, or a pharmaceutically acceptable salt thereof.

* * * * *